United States Patent
Gupta (10) Patent No.: US 9,095,457 B2
(45) Date of Patent: Aug. 4, 2015

(54) ANTI-MIGRATION BILIARY STENT AND METHOD

(71) Applicant: Cook Medical Technologies LLC, Bloomington, IN (US)

(72) Inventor: Kapil Gupta, Los Angeles, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 74 days.

(21) Appl. No.: 13/940,810

(22) Filed: Jul. 12, 2013

(65) Prior Publication Data

US 2014/0025180 A1   Jan. 23, 2014

Related U.S. Application Data

(60) Provisional application No. 61/673,995, filed on Jul. 20, 2012.

(51) Int. Cl.
*A61F 2/04*  (2013.01)
*A61F 2/82*  (2013.01)
*A61F 2/94*  (2013.01)

(52) U.S. Cl.
CPC ... *A61F 2/82* (2013.01); *A61F 2/04* (2013.01); *A61F 2/94* (2013.01); *A61F 2002/041* (2013.01); *A61F 2220/0016* (2013.01); *A61F 2230/0041* (2013.01); *A61F 2250/0098* (2013.01)

(58) Field of Classification Search
CPC .......................................................... A61F 2/04
USPC ................................ 623/23.64–23.7; 604/8–9
See application file for complete search history.

(56) References Cited

U.S. PATENT DOCUMENTS

| | | | | |
|---|---|---|---|---|
| 8,221,505 | B2 * | 7/2012 | Skerven | 623/23.68 |
| 8,603,185 | B2 * | 12/2013 | Shah et al. | 623/23.64 |
| 2003/0109930 | A1 * | 6/2003 | Bluni et al. | 623/23.7 |
| 2003/0199986 | A1 * | 10/2003 | McWeeney et al. | 623/23.7 |
| 2005/0240278 | A1 * | 10/2005 | Aliski et al. | 623/23.7 |
| 2008/0234659 | A1 * | 9/2008 | Cheng et al. | 604/523 |

(Continued)

FOREIGN PATENT DOCUMENTS

WO    WO 2009/029744 A1    3/2009

OTHER PUBLICATIONS

International Search Report mailed Sep. 12, 2013 for International Application No. PCT/US2013/050188.
Written Opinion of the International Searching Authority mailed Sep. 12, 2013 for International Application No. PCT/US2013/050188.

*Primary Examiner* — Suzette J Gherbi
(74) *Attorney, Agent, or Firm* — Brinks Gilson & Lione (57) ABSTRACT

A stent and a method for implanting the stent are provided. The stent includes a generally tubular body having a lumen defined therethrough. The body includes a proximal portion having a curved portion where the curved portion is configured for placement proximal to a sphincter. The body also includes a substantially straight distal portion having first and second retaining members. The second retaining member is positioned on the distal portion and the first retaining member is positioned proximal to the second retaining member. The first and second retaining members are positioned on a common longitudinal axis extending along a wall of the distal portion and the first and second retaining members extend away from the body in a common direction so that a free end of the first retaining member and a free end of the second retaining member extend away from a distal end of the body.

19 Claims, 7 Drawing Sheets

(56) References Cited

U.S. PATENT DOCUMENTS

| | | | |
|---|---|---|---|
| 2009/0105719 A1* | 4/2009 | Honey et al. | 606/108 |
| 2010/0114325 A1* | 5/2010 | Yang et al. | 623/23.7 |
| 2010/0145467 A1* | 6/2010 | Davoudi et al. | 623/23.7 |
| 2010/0211098 A1* | 8/2010 | Hadba et al. | 606/232 |
| 2011/0224775 A1 | 9/2011 | Shah et al. | |
| 2012/0095545 A1 | 4/2012 | Yamagata | |
| 2012/0165956 A1* | 6/2012 | Li | 623/23.66 |

* cited by examiner

ANTI-MIGRATION BILIARY STENT AND METHOD

RELATED APPLICATIONS

This application claims the benefit of U.S. Provisional Application No. 61/673,995, filed Jul. 20, 2012, which is incorporated by reference herein in its entirety.

TECHNICAL FIELD

This invention generally relates to stents that are implantable in a vessel or duct within the body of a patient, and in particular to stents that may be used to maintain patency of the vessel or duct in the biliary system.

BACKGROUND

Prosthetic devices may be placed in vessels and ducts for a number of medical procedures. Typically, placement of the prosthetic devices into the vessels and ducts functions to maintain an open passage through the vessel or duct. For example, where a biliary or pancreatic duct becomes occluded, it is often desirable to facilitate drainage through the duct by the placement of a tubular prosthesis within the occluded area. In some embodiments, one or more stents have been used to maintain an open passage.

The passageways into which the stents are placed may change shape and move in response to bodily movement of the patient. Stents designed for placement in these passageways are flexible to accommodate movement of the passageway. Stents are commonly made of polymers or metals, typically a shape memory ahoy, and may include flaps or barbs at each end of the stent which serve to prevent migration and retain the stent in place. Some stents may have various preformed retaining configurations, such as pigtails or spirals, to help maintain the stent in position. Stents have also been formed into various expandable configurations so that, when the stent has reached the occluded area, the stent is expanded to press outwardly against the ductal wall and to thereby maintain its position within the duct.

During the placement procedure, especially when more than one stent is being positioned within the duct, the stents may change position. For example, when one stent is positioned within the duct and a second stent is placed beside the first stent, the first stent may be pushed too far into the duct during positioning of the second stent.

There is a need for an improved stent which can be atramatically placed within duct and that can be maintained in position or easily repositioned when additional stents are placed within the same duct.

SUMMARY OF THE INVENTION

Accordingly, it is an object of the present invention to provide a stent and method having features that resolve or improve on one or more of the above-described drawbacks.

The foregoing object is obtained in one aspect of the present invention by providing a stent and a method for implanting the stent. The stent includes a generally tubular body having a lumen defined therethrough. The body includes a proximal portion having a curved portion where the curved portion is configured for placement proximal to a sphincter. The body also includes a substantially straight distal portion having first and second retaining members. The second retaining member is positioned on the distal portion and the first retaining member is positioned proximal to the second retaining member. The first and second retaining members are positioned on a common longitudinal axis extending along a wall of the distal portion and the first and second retaining members extend away from the body in a common direction so that a free end of the first retaining member and a free end of the second retaining member extend away from a distal end of the body.

DETAILED DESCRIPTION OF THE EMBODIMENTS

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient using a deployment system. Hence the term distal means the portion of the stent that is farthest from the physician and the term proximal means the portion of the stent that is nearest to the physician.

Figure 1:
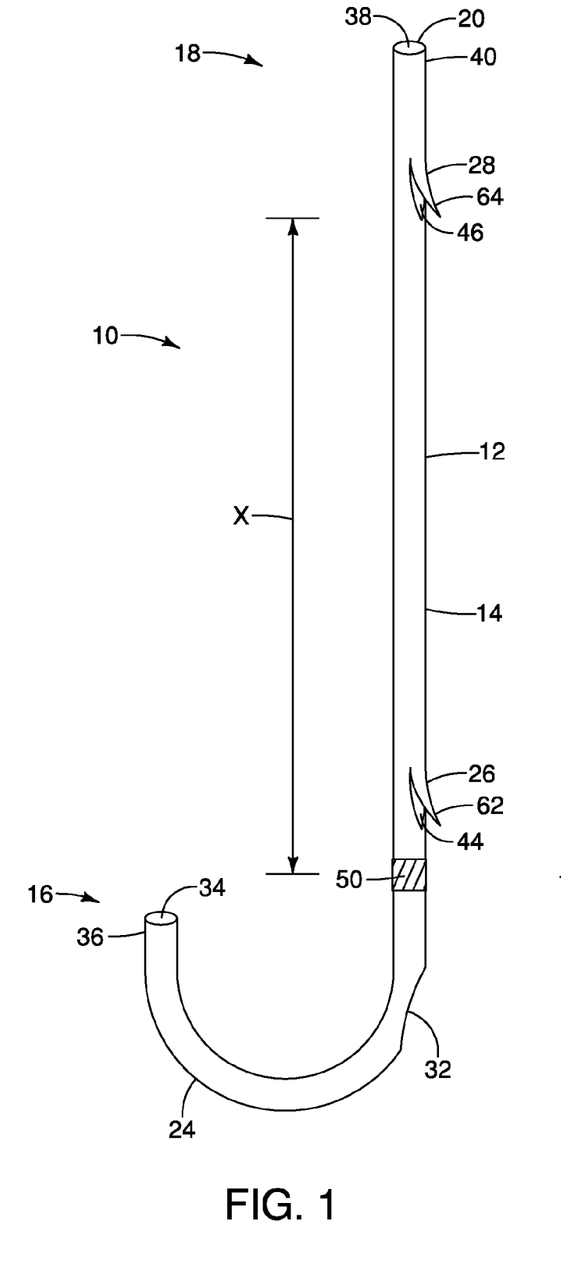
FIG. 1 is a side view of an embodiment of a stent according to the present invention.
Figure 2:
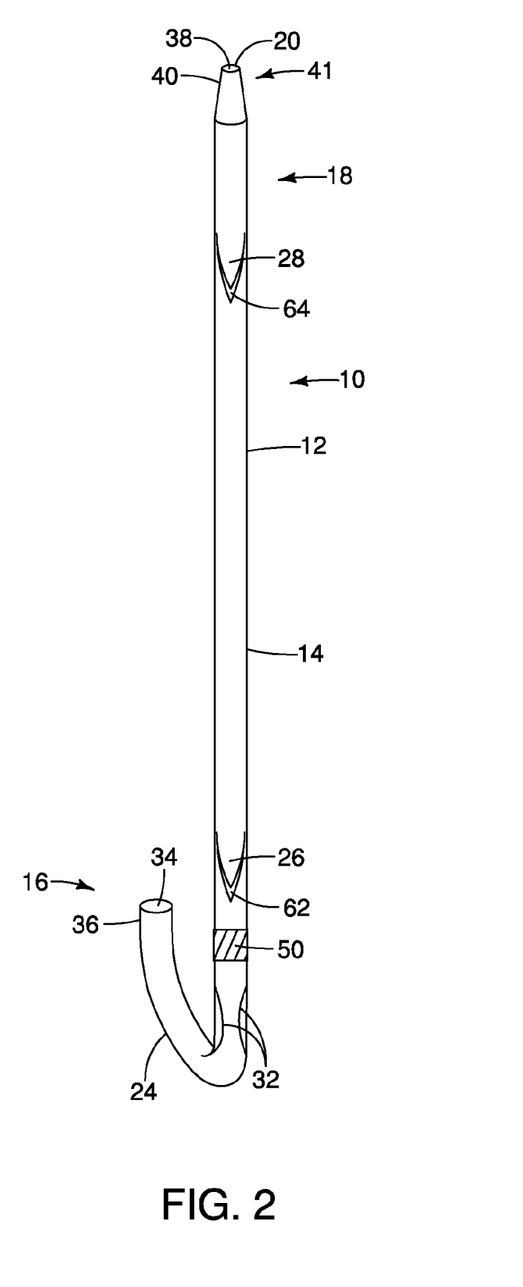
FIG. 2 is a perspective view of an embodiment of the stent of the present invention.

FIGS. 1 and 2 illustrate a stent 10 in accordance with embodiments of the present invention. In some embodiments, the stent 10 is a non-expandable stent. The stent 10 includes a generally tubular body 12 having a proximal portion 16 and a distal portion 18. A lumen 20 extends through at least a portion of the tubular body 12 of the stent 10. The body 12 includes a substantially straight portion 14 connected to a curved portion 24. The substantially straight portion may conform to the contours of the duct when the stent 10 is implanted. The term "substantially straight" refers to a portion that is free of loops, such as the curve formed at the curved portion 24. The curved portion 24 is formed in the proximal portion 16 and is configured for placement proximal to a sphincter as described in more detail below. In some embodiments, the curved portion 24 is C-shaped although other shapes are also possible. The body 12 also may include a first retaining member 26 and a second retaining member 28 that extend radially away from a longitudinal axis of the substantially straight portion 14 of the body 12. The second retaining member 28 is positioned on the distal portion 18 of the stent 10 and the first retaining member 26 is positioned proximal to the second retaining member 28. The retaining members 26, 28 may extend radially outward at an angle of about 5-90° relative to the body 12. The length of the retaining member may be about 4 mm to about 15 mm, although other lengths are possible, and may depend on the size of the duct, the size of the obstruction and the size of the stent. The retaining members 26, 28 may be formed by any method known to one skilled in the art, for example, by skiving or molding.

The stent 10 also includes at least one opening 32 in the proximal portion 16 of the body 12 connected to the lumen 20 that is configured to allow drainage out of the lumen 20. As shown in FIG. 1, the opening 32 may be formed in the curved portion 24. The stent 10 may also include a proximal opening 34 at a proximal end 36 of the stent 10 and a distal opening 38 at a distal end 40 of the stent 10. The proximal and distal openings 34, 38 are connected to the lumen 20. In some embodiments, the opening 32 may be positioned to align with the lumen 20 extending along the substantially straight portion 14 to facilitate drainage of the lumen 20. In the embodiment shown in FIG. 1 having a C-shaped curved portion 24, the proximal and distal openings 34, 38 are oriented in the same direction.

Figure 4:
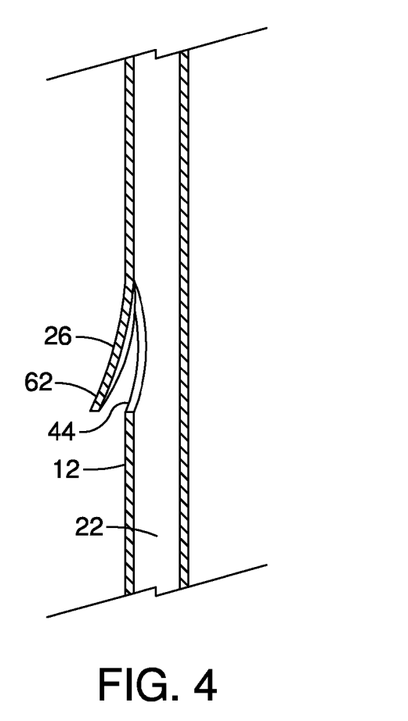
FIG. 4 is a cross-sectional view of the retaining member of a stent.

The body 12 of the stent 10 may also include a first opening 44 formed at the first retaining member 26 and a second opening 46 formed at the second retaining member 28. The first and second openings 44, 46 may be formed by skiving the body 12 of the stent 10 to form the retaining members 26, 28 where the skived portion is sufficiently thick to cut through the body 12 and form the openings 44, 46. An enlarged view of the skived opening 44 is shown in FIG. 4. In some embodiments, the skived retaining members 26, 28 may be formed by skiving but without cutting through the entire thickness of the wall and forming an opening in the body 12. The body 12 of the stent 10 extending between the retaining members 26, 28 (and openings 44, 46 when present) is a dosed tubular structure free from openings.

Figure 3:
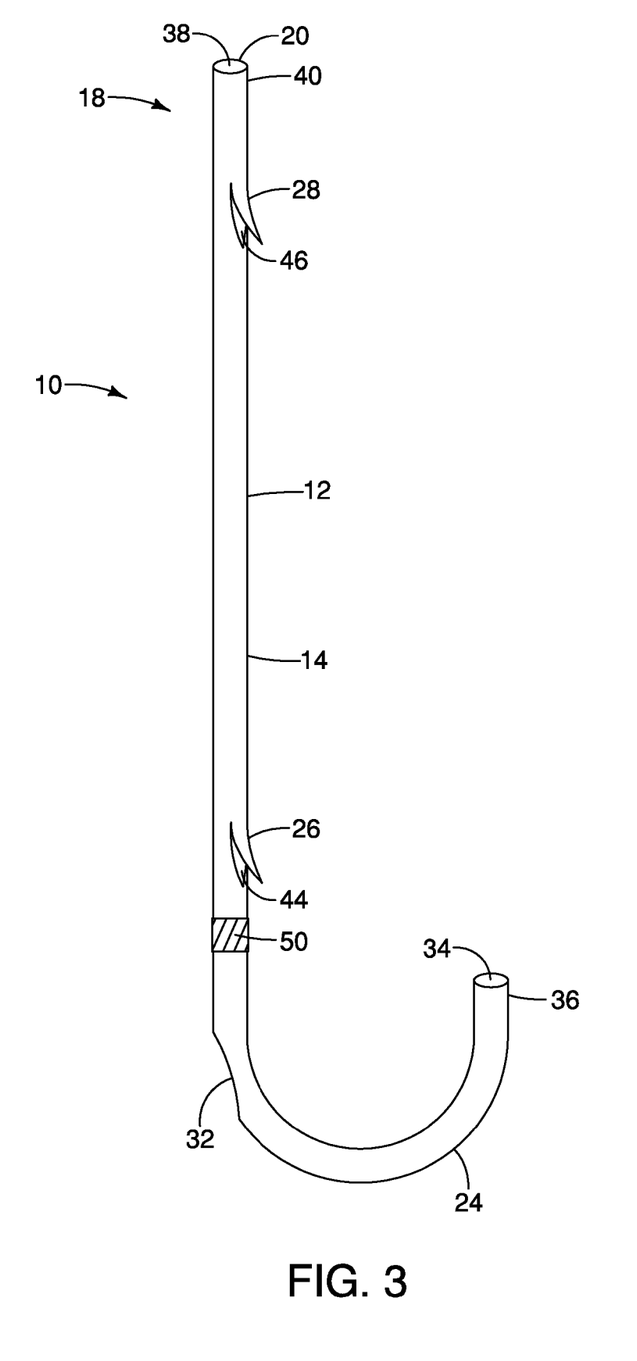
FIG. 3 is a side view of an alternative embodiment of the stent of the present invention.

As shown in FIG. 1, both the first and second retaining members 26, 28 extend outward from the same side of the stent 10. The first and second retaining members 26, 28 also extend in the same direction. As shown in FIG. 1, a free end 62 of the first retaining member 26 and a free end 64 of the second retaining member 28 extend away from the distal portion 18 of the stent 10. The direction of the retaining members 26, 28 shown in FIG. 1 allows the retaining members 26, 28 to hold the stent 10 in position within the biliary duct and to inhibit the stent 10 from migrating out of the duct. The direction of the curved portion 24 allows the curved portion 24 to help hold the proximal portion 16 in the duodenum and to help keep the stent 10 from complete insertion within the biliary duct as discussed in more detail below. In some embodiments, the retaining members 26, 28 may be off-set from alignment with the curved portion 24. In some embodiments, the first and second retaining members 26, 28 may be on an opposite side of the stent 10 to the curved portion 24 as shown in FIG. 1. In some embodiments, the first and second retaining members 26, 28 may be on the same side of the stent 10 as the curved portion 24 and aligned on a common longitudinal axis with the retaining members 26, 28 as shown in FIG. 3.

The body 12 may include one or more radiopaque markers 50 to be visualized using fluoroscopy or x-ray. In some embodiments, the marker 50 may be positioned proximal to the first retaining member 26 to facilitate positioning of the stent 10 within the duct as described in more detail below. In some embodiments, the radiopaque marker 50 may be provided on the body 12 between the curved portion 24 and the first retaining member 26. In some embodiments, the stent 10 may also include additional markers 50, for example to indicate the position of the second retaining member 28 and/or the distal end 40. In some embodiments, the stent 10 itself may be formed from a radiopaque material. Some embodiments may include visual markings created by a laser or ink that may be visualized so the stent 10 may be visualized using fluoroscopy or x-ray.

In some embodiments, the distal portion 18 of the body 12 may include a tapered end 41 as shown in FIG. 2. Also as shown in FIG. 2, the proximal portion 14 may include two openings 32 to facilitate drainage from the duct through the stent 10. The openings 32 may be positioned adjacent to each other, proximal to the marker 50 and distal to the proximal end 36.

The stent 10 may be of any size suitable for implantation into a duct or passageway such as the biliary ducts. The stent 10 may have an outer diameter of about 7-10 Fr, although other sized stents may also be used. The length of the stent 10 will generally depend on the position of the obstruction within the duct. The stent 10 may be supplied in about 2 cm increments so that the second retaining member 28 may be positioned distal to the obstruction to help prevent the stent 10 from migrating out of the duct. By way of non-limiting example, the distance x from the radiopaque marker 50 to the second retaining member 28 may be about 2, 4, 6, 8, 10 or 12 cm, depending on the position of the obstruction. Shorter or longer stents may also be used.

The stent may be made from materials so that the stent is soft enough to conform to the curvature of the duct and eliminate or reduce irritation at the implantation site that occurs with a rigid stent. The materials should also have sufficient strength to maintain a lumen through the stent when the stent is positioned within the duct. Suitable materials for the stent of the present invention include, but are not limited to the following, SOF-FLEX™, a type of polyether urethane, silicone, block co-polymers, urethanes, polyethylene, polystyrene, polytetrafluoroethylene (PTFE), FEP and the like and combinations thereof.

Figure 5:
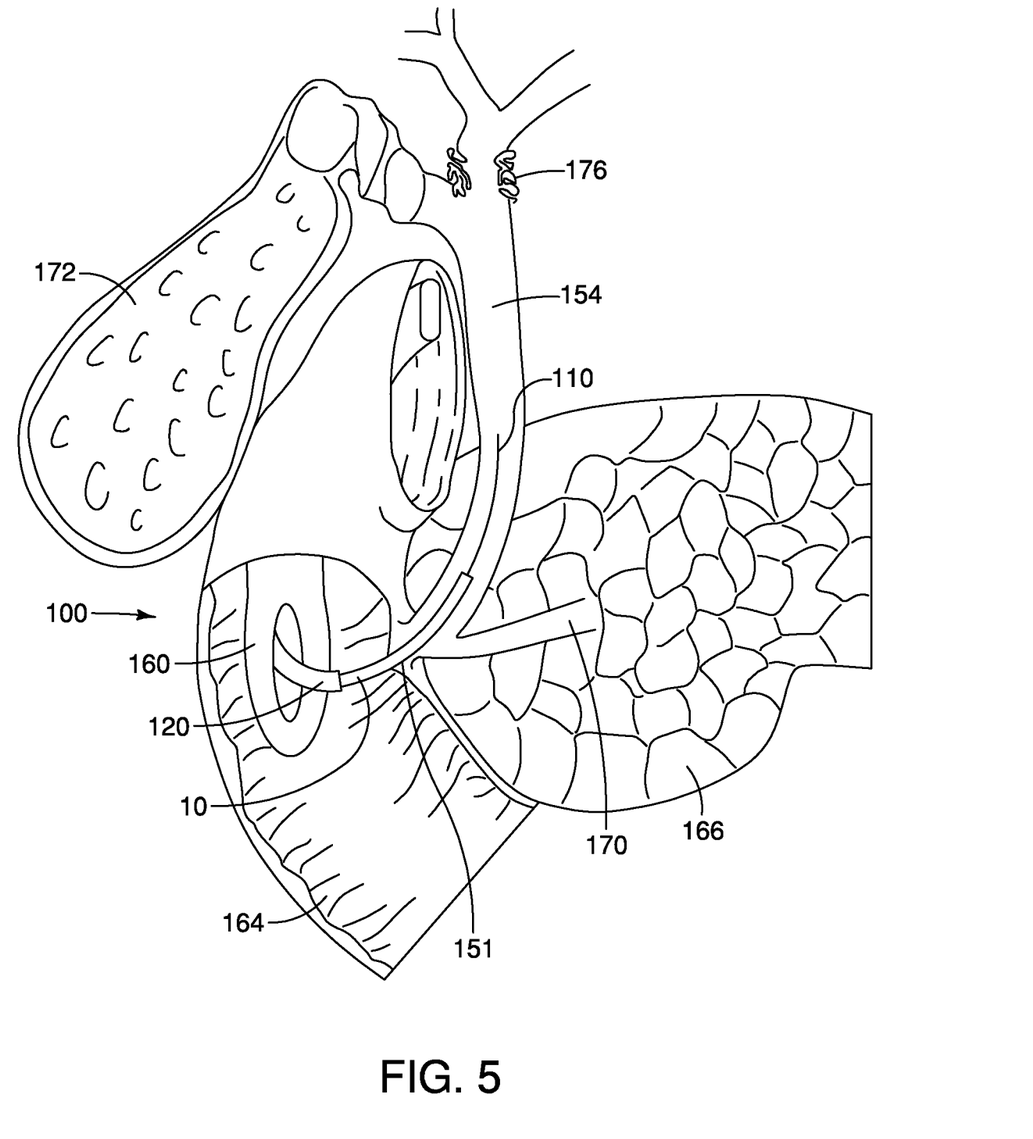
FIG. 5 is a diagrammatic view of an embodiment of the stent being delivered to a biliary duct.

The stent 10 may be delivered to the implantation site using any delivery system known in the art. The delivery system used will depend on the size of the stent 10 and the materials used to form the stent 10. FIG. 5 illustrates an exemplary delivery system 100. The delivery system 100 includes a wire guide 110 and an introducer catheter 120. The wire guide 110 extends through a lumen 122 in the introducer catheter 120 and the lumen 20 in the stent 10 for directing the delivery of the stent 10 through the passageways to the body site for placement of the stent 10. During delivery to the site, the stent 10 is placed over the wireguide 110 and the curved portion 24 of the stent 10 is temporarily straightened. Once the wire guide 110 and the introducer catheter 120 have been removed from the stent 10 at the delivery site, the curved portion 24 resumes the curved configuration. The delivery system 100 may also include additional lumens.

An exemplary method of delivering and implanting the stent 10 of the present invention will be illustrated with reference to the delivery system 100. As shown in FIG. 5, the delivery system 100 may be used to place the stent 10 through the Sphincter of Oddi 151. As shown in FIG. 5, the wireguide 110 has been advanced through the Sphincter of Oddi 151 and into the common bile duct 154. The duodenum 164, the pancreas 166, the pancreatic duct 170 and the gall bladder 172 are also shown for reference. The stent 10 is advanced over the wireguide 110 and out of an endoscope 160 by the introducer catheter 120. The introducer catheter 120 advances the stent 10 into position by pushing the stent 10 distally along the wireguide 110 until the implantation site is reached. In some embodiments, the stent 10 may be delivered using an outer sheath positioned over the delivery catheter 120 and the stent 10 (not shown).

Figure 6:
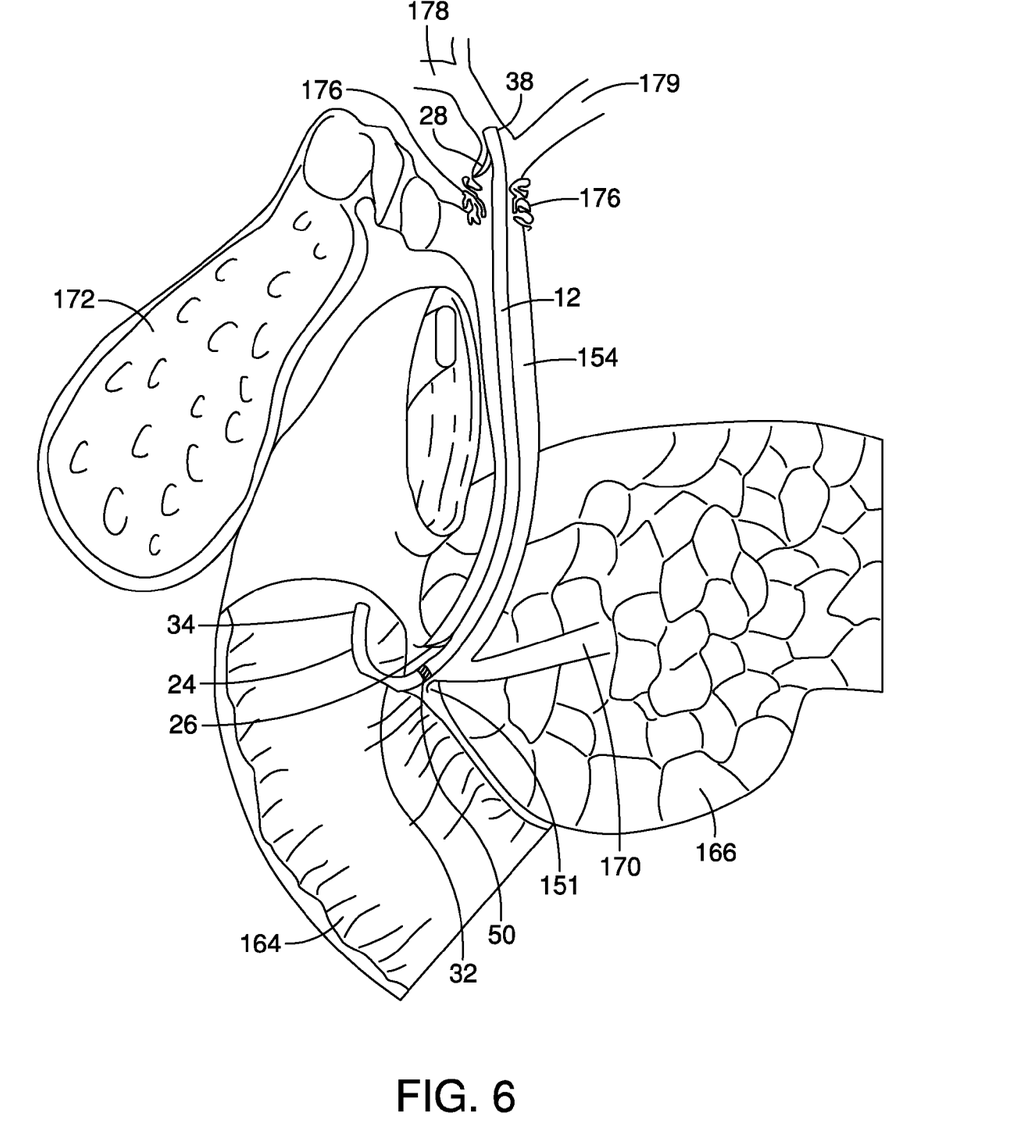
FIG. 6 is a diagrammatic view of a first stent placed within the biliary duct.

As shown in FIG. 6, the stent 10 may be advanced until the first retaining member 26 is through the sphincter 151 and expands outward to contact the sphincter 151. The distal portion 38 of the stent 10 is advanced though a stricture or lesion 176 in the duct 154, for example a tumor growing into the duct 154, so that the second retaining member 28 is positioned distal to the stricture 176. The distal portion 38 may be positioned within the right hepatic duct 178 as shown in FIG. 6. In this position, the second retaining member 28 helps to keep the stent 10 from migrating out of the duct 154 by providing resistance against the stricture 176. The first retaining member 26 also helps to keep the stent 10 from migrating out of the duct 154 by providing resistance against the sphincter 151. The radiopaque marker 50 may be used to help position of the stent 10 within the duct 154. Once the stent 10 is positioned within the duct 154, the wireguide may be withdrawn from the stent 10 and the curved portion 24 returns to the curved configuration with the curved portion 24 positioned in the duodenum 164. The opening 32 is positioned within the duodenum 164 so that bile can drain from the ducts 154, 178 through the lumen 20 of the stent 10 and out of the opening 32.

Figure 7:
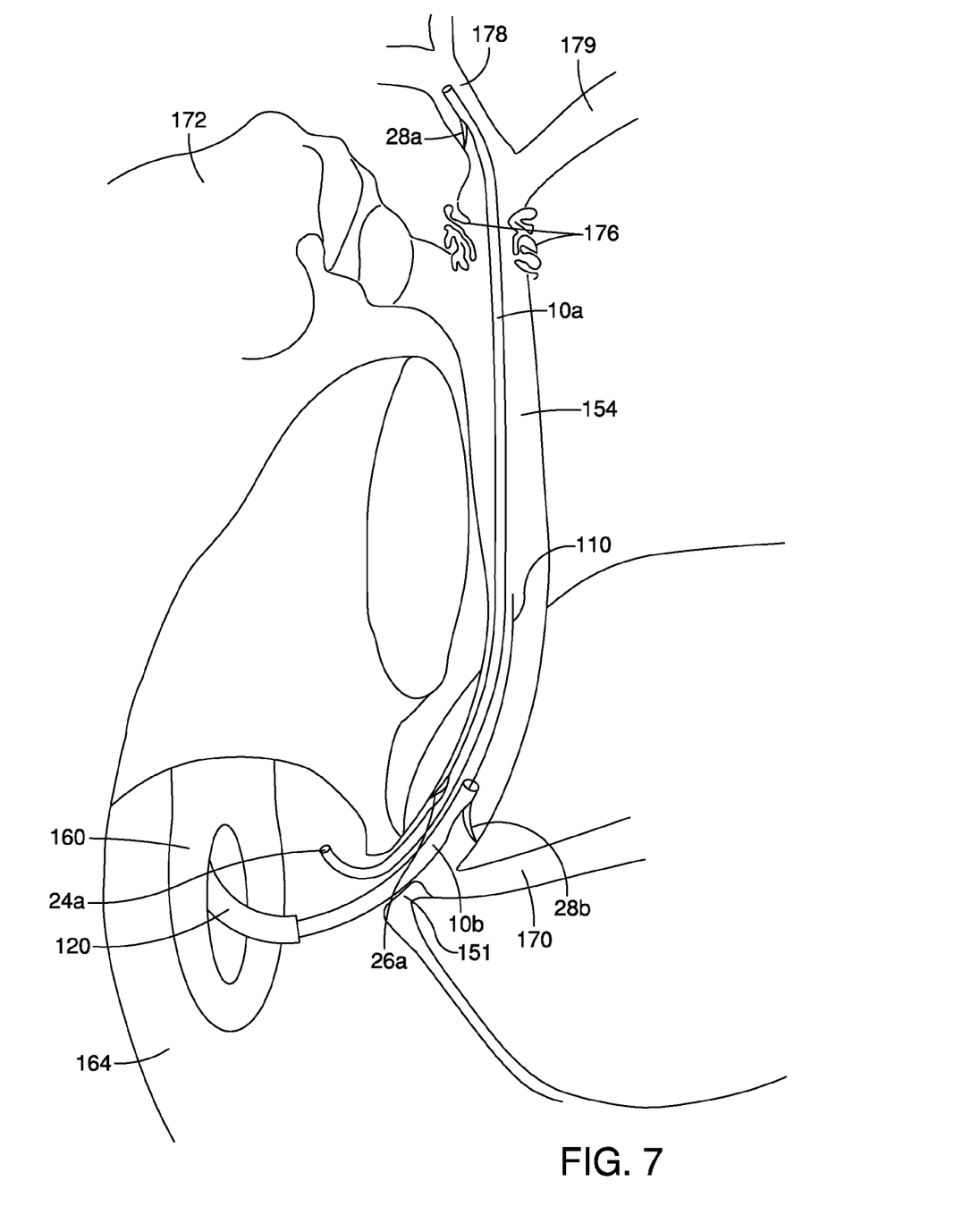
FIG. 7 is an enlarged diagrammatic view of a second stent being delivered to the biliary duct.

As shown in the enlarged view in FIG. 7, a second stent 10 may be positioned within the biliary duct 154 to further facilitate drainage of the bile past the obstruction 176 in the duct 154. The first stent 10a has been positioned within the duct 154 with the distal portion 38a positioned in the right hepatic duct 178. The second stent 10b is delivered to the biliary duct 154 using the wire guide 110 and the delivery catheter 120 as described above. As shown in FIG. 7, one problem with the delivery of the second stent 10b is that the first stent 10a gets pushed distally into the duct 154 as the second stent 10b pushes past the first stent 10a. As shown in FIG. 7, the first and second retaining members 26a, 28a of the first stent 10a are distal to the sphincter 151 and the stricture 176, respectively due to the first stent 10a being pushed distally by the second stent 10b. The curved portion 24a may be held or used to reposition the first stent 10a as the second stent 10b is positioned within the duct 154 as shown in FIG. 8.

Figure 8:
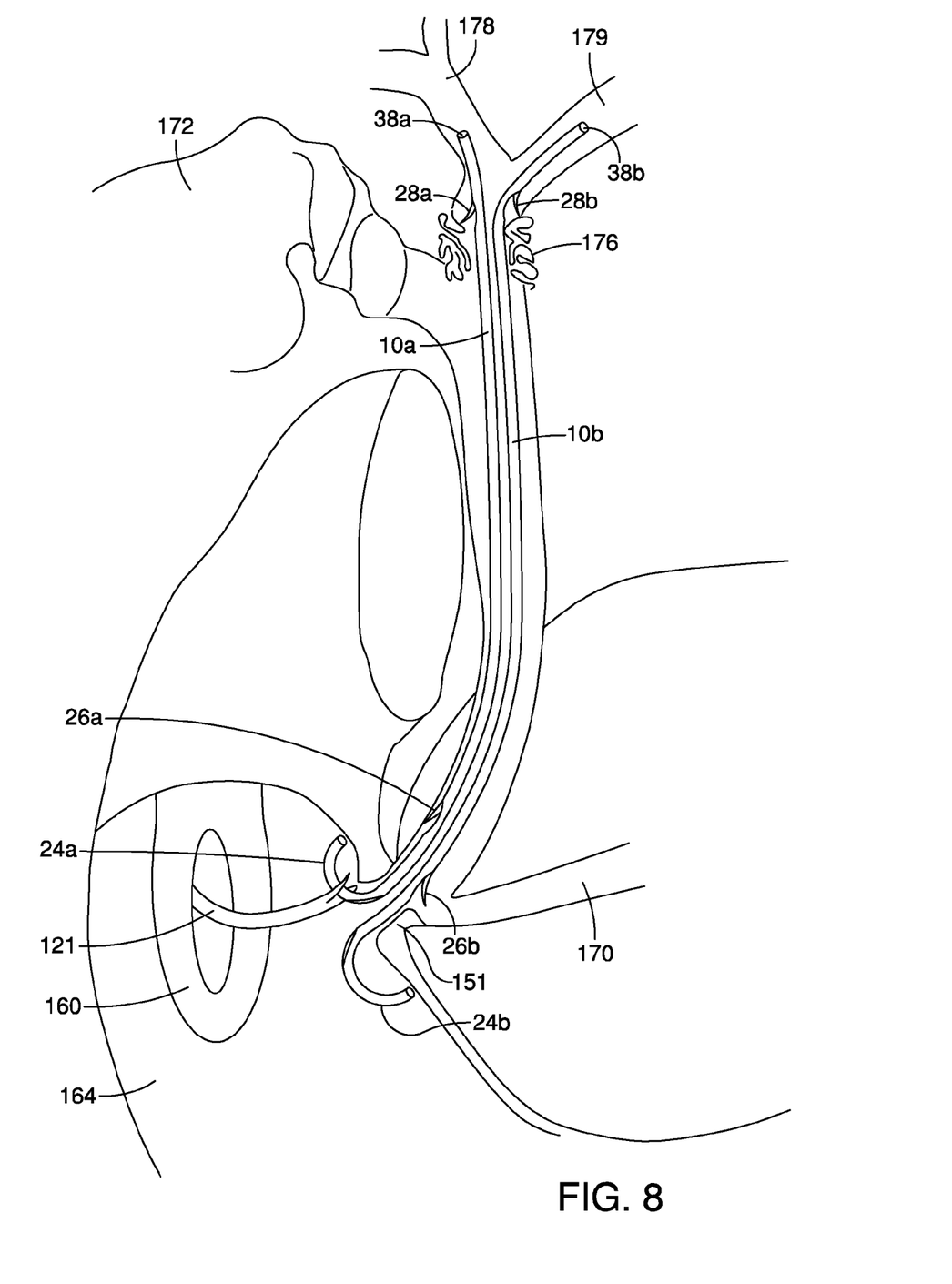
FIG. 8 is an enlarged diagrammatic view of the first stent and the second stent in the biliary duct.

As shown in FIG. 8, the first stent 10a may be positioned so that the distal portion 38a of the first stent 10a is positioned in the right hepatic duct 178. The second stent 10b may be positioned so that the distal portion 38b of the second stent 10b is positioned in the left hepatic duct 179. Both curved portions 24a, 24b of the first and second stents 10a, 10b may be positioned within the duodenum 164. Additional stents 10 may also be placed within the biliary duct 154 using the procedure described a above. The curved portion 24 of each stent may be used to hold the position or to reposition the stent 10 so that each stent 10 is properly positioned to facilitate drainage of bile.

Figure 9:
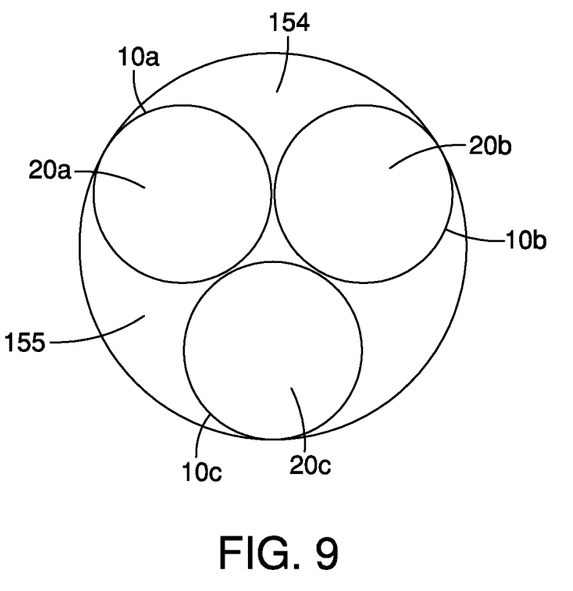
FIG. 9 is a cross sectional view of a plurality of stents placed in the biliary duct.

With two or more stents 10 placed within the biliary duct 154 and extending to the duodenum 164, drainage of bile is also facilitated around and between the stents 10. The stents 10 help to maintain the patency of the duct 154 so that the bile can drain through the stent lumens 20 or in the spaces provided by adjacent stents. A cross sectional view through the duct 154 is shown in FIG. 9, illustrating the spaces through which the bile can drain. As shown in FIG. 9, bile may drain through each lumen 20 and or through a lumen 155 of the duct 154 held open between the stents 10. While three stents 10 are illustrated in FIG. 9, 1, 2, 3, 4 or more stents 10 may be placed within the duct 154 depending on the size of the stent and the diameter of the duct 154. By way on non-limiting example, if a 10 Fr stent is used, 2-3 stents may be positioned within the duct 154. If a 7 Fr stent is used, 4-5 stents may be positioned within the duct 154. A combination of different sized stents may also be used and the number of stents placed in the duct will vary based on the sizes of the stents and the size of the duct.

The above Figures and disclosure are intended to be illustrative and not exhaustive. This description will suggest many variations and alternatives to one of ordinary skill in the art. All such variations and alternatives are intended to be encompassed within the scope of the attached claims.

The invention claimed is:

1. A non-expandable stent comprising:
a generally tubular body having a lumen defined therethrough, the body comprising:
a proximal portion comprising a curved portion formed from the tubular body and a proximal end opening at an end of the curved portion so that the end of the curved portion is distal to a mid-portion of the curved portion, the curved portion configured for placement proximal to a sphincter; and
a substantially straight distal portion comprising a first retaining member and a second retaining member, the second retaining member positioned on the distal portion and the first retaining member positioned proximal to the second retaining member, the first and second retaining members positioned on a common longitudinal axis extending along a wall of the distal portion and the first and second retaining members extending away from the body in a common direction so that a free end of the first retaining member and a free end of the second retaining member extend away from a distal end of the body.

2. The stent of claim 1, wherein the first and second retaining members are offset from alignment with the curved portion.

3. The stent of claim 2, wherein the first and second retaining members are offset about 180° circumferentially from the curved portion.

4. The stent of claim 1, wherein the curved portion is c-shaped.

5. The stent of claim 1, wherein the first and second retaining members formed by skiving a portion of the tubular body.

6. The stent of claim 1, wherein the body is free of openings between the first retaining member and the second retaining member.

7. The stent of claim 1, wherein the body comprises an opening in the curved portion proximal to the first retaining member.

8. The stent of claim 7, wherein the body comprises a second opening in the curved portion proximal to the first retaining member.

9. The stent of claim 1, wherein the body comprises a distal end opening, the distal and proximal end openings oriented in the same direction.

10. The stent of claim 1, further comprising a radiopaque marker positioned proximal to the first retaining member.

11. The stent of claim 1, comprising a distance x extending longitudinally between a radiopaque marker and the second retaining member, wherein the distance x is between about 2-12 cm.

12. The stent of claim 1, wherein the stent comprises a material selected from the group consisting of plastics, silicone, block polymers, urethanes, polystyrene, polyethylene, PTFE, FEP and combinations thereof.

13. The stent of claim 1, further comprising a tapered distal end.

14. A non-expandable stent comprising:
a generally tubular body having a lumen defined therethrough, the body comprising:
a proximal portion comprising a curved portion formed from the tubular body and a proximal end opening, the curved portion configured for placement proximal to a sphincter; and
a substantially straight distal portion comprising a first retaining member and a second retaining member, the second retaining member positioned on the distal portion and the first retaining member positioned proximal to the second retaining member, the first and second retaining members extending away from the body in a common direction so that a free end of the first retaining member and a free end of the second retaining member extend away from a distal end of the body, the body comprising an opening in the curved portion proximal to the first retaining member and distal to the proximal end opening, the opening aligned with a longitudinal axis of the lumen in the distal portion.

15. The stent according to claim 14, further comprising a second opening in the curved portion proximal to the first retaining member.

16. The stent according to claim 14, wherein the first and second retaining members are on a same side of the distal portion.

17. The stent according to claim 14, wherein the curved portion is c-shaped.

18. The stent according to claim 14, wherein the first and second retaining members are offset from alignment with the curved portion.

19. The stent according to claim 1, wherein the curved portion is aligned on the common longitudinal axis with the first and second retaining members so that the curved portion and the first and second retaining members extend out from the longitudinal axis in a same side of the stent.

* * * * *